United States Patent [19]

Loev et al.

[11] Patent Number: 4,505,930
[45] Date of Patent: Mar. 19, 1985

[54] ALPHA-ALKYL POLYOLEFINIC CARBOXYLIC ACIDS AND DERIVATIVES THEREOF USEFUL IN THE TREATMENT OF PSORIASIS AND ALLERGIC RESPONSES

[75] Inventors: Bernard Loev, Scarsdale; Wan-Kit Chan, Yorktown Heights; Howard Jones, Ossining, all of N.Y.

[73] Assignee: USV Pharmaceutical Corporation, Tarrytown, N.Y.

[21] Appl. No.: 511,822

[22] Filed: Jul. 8, 1983

Related U.S. Application Data

[63] Continuation-in-part of Ser. No. 392,837, Jun. 28, 1982, Pat. No. 4,472,438.

[51] Int. Cl.³ .................... A61K 31/16; A61K 31/20; A61K 31/23; A61L 9/04
[52] U.S. Cl. ..................................... 514/529; 424/45; 514/557; 514/613
[58] Field of Search ................. 424/312, 318, 320, 45

[56] References Cited

U.S. PATENT DOCUMENTS 3,934,028 1/1976 Lee .......................... 424/318
4,021,573 5/1977 Lee .......................... 424/318

Primary Examiner—Stanley J. Friedman

[57] ABSTRACT

Polyolefinic compounds represented by the general formula

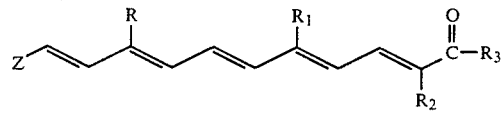

in which R and $R_1$ are each hydrogen or an alkyl group of from 1 to 5 carbon atoms; $R_2$ is an alkyl group of from 1 to 5 carbon atoms; $R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl or trifluoromethyl groups or halogen atoms or combinations thereof and the pharmaceutically-acceptable salts thereof.

The foregoing compounds have been found to be effective in the treatment of psoriasis, inflammatory conditions and allergic responses.

18 Claims, No Drawings

ALPHA-ALKYL POLYOLEFINIC CARBOXYLIC ACIDS AND DERIVATIVES THEREOF USEFUL IN THE TREATMENT OF PSORIASIS AND ALLERGIC RESPONSES

BACKGROUND OF THE INVENTION

This is a continuation-in-part application of application Ser. No. 392,837, filed June 28, 1982, now U.S. Pat. No. 4,472,430.

The present invention relates to novel alpha-alkyl polyolefinic carboxylic acids derived from such polyolefinic intermediates as retinal(3,7-dimethyl-9-(2,6,6-trimethyl-1-cyclohexen-1-yl)-2,4,6,8-nonatetraenal; vitamin A aldehyde) which possesses the structure

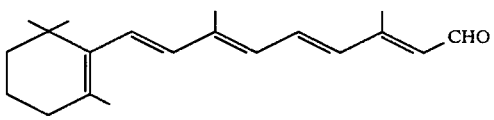

A synthesis of retinal from beta-ionone and propargyl halide is described in U.S. Pat. No. 3,060,229.

A number of alpha-substituted polyolefinic carboxylic aldehydes, acids and esters are described in the scientific literature. Japanese Pat. No. 10,124 (1964); C.A. 62, 2798 g (1965) describes 2,7-dimethyl-9-(2,6,6-trimethyl-1-cyclohexen-1-yl)-2,4,6,8-nonatetraenonic acid and 2,7,11-trimethyl-13-(2,6,6-trimethyl-1-cyclohexen-1-yl)-2,4,6,8,10,12-tridecahexanenoic acid; Machleidt, et al., *Justus Liebigs Ann. Chem.*, 679,20 (1964) describes α-fluoropolyolefinic acids and esters; Chan, et al., *J.A.C.S.* 96, 3642 (1974) describe polyolefinic carboxyaldehydes; Haeck, et al., *Recuil* 85 (1966) pp. 334–338 describe 5,9-dimethyl-11-(2,6,6-trimethyl-1-cyclohexen-1-yl)-2,4,6,8,10-undecapentaenoic acid and corresponding 2,4,6,8,10,12-tridecahexaneoic acids as well as the corresponding α-cyano and α-carboxy substituted compounds. Buchta, et al., *Naturwissenschaften* 46, 74 (1959) describe methyl-2-methyl-7-phenyl)-2,4,6-heptatrienoate.

SUMMARY OF THE INVENTION

The present invention is directed to novel alpha-alkyl, polyolefinic carboxylic acids and derivatives thereof of the general formula

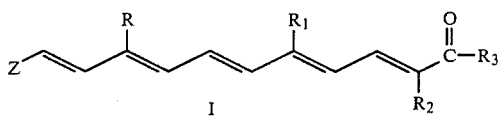

I in which R and $R_1$ are each hydrogen or an alkyl group of from 1 to 5 carbon atoms; $R_2$ is an alkyl group of from 1 to 5 carbon atoms; $R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group, or a phenyl group substituted with from 0 to 4 hydroxy, alkoxy, alkyl or trifluoromethyl groups or halogen atoms or combinations thereof; and the pharmaceutically-acceptable salts thereof. The invention includes compounds wherein the double bonds are in the cis or trans configuration.

The foregoing compounds have been found to be effective in the treatment of psoriasis, acne, and cellular and humoral immunodeficiency.

Compounds of the foregoing invention have also been found active in regulating the formation of lipoxygenase and as such possess therapeutic value in the treatment of inflammatory conditions and allergic responses.

DESCRIPTION OF THE PREFERRED EMBODIMENTS

A preferred group of compounds within the aforesaid general formula are those in which $R_1$ is methyl, $R_3$ is hydroxyl or alkoxy of from 1 to 5 carbon atoms and Z is a cycloalkenyl group substituted with from 0 to 3 alkyl groups, or a phenyl group substituted with from 1 to 4 alkoxy or alkyl groups containing up to 5 carbon atoms or combinations of the foregoing, including those compounds in which one or more of the double bonds are in the cis configuration. Within this preferred group of compounds, still more preferred are compounds in which Z is the group 2,6,6-trimethyl-1-cyclohexen-1-yl.

The compounds of this invention can be prepared from known polyolefinic materials, e.g., retinal, employing known synthetic procedures of from analogous polyolefinic compounds which can be prepared in accordance with methods known by those skilled in the art.

For example, employing retinal as starting compound, condensation through the aldehyde group with the active methylene group of suitable acids or acid derivatives of the formula:

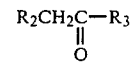

will result in the corresponding undecapentaenoic acid derivative. Activating substituents on the alpha carbon atom of the said compounds, e.g., trialkylphosphono derivatives, facilitate the condensation reaction.

The condensation reaction is usually carried out by reacting the selected starting materials in a suitable solvent preferably in the presence of a strong base such as sodium hydride, sodamide, sodium ethoxide and similar alkali metal compounds. The reaction is usually exothermic and is consequently cooled to control the rate of reaction. After the initial reaction has subsided, the reaction mixture is heated at reflux to assure completeness of reaction.

A variety of reaction solvents can be employed including dioxane, tetrahydrofuran (THF), dimethylformamide, dimethylacetamide and similar water-miscible organic solvents. The solvents employed are preferably anhydrous, particularly when the alkali metal bases are used, to avoid secondary reactions.

The present new compounds can also be prepared from corresponding compounds containing only alpha hydrogen by alkylation using alkylating agents such as dialkyl sulfates, e.g., dimethyl and diethyl sulfate and alkyl halides, e.g., propyl bromide and ethyl bromide, in the presence of alkali metals or alkali metal compounds which react with alpha halogen, e.g., sodium hydride, lithium, potassium, sodamide and alkali metal alkoxides such as sodium or potassium ethoxide.

The compounds of this invention are also prepared by partial reduction of corresponding compounds containing acetylenic in lieu of ethylenic bonds. In addition, the dehydrohalogenation of corresponding alpha-halo acid with no ethylenic bond between alpha and beta carbon atoms also leads to the present compounds.

A further preparative method involves condensation of appropriate side chains with the appropriate side chains with the appropriately substituted cyclohexanone with, for example, an omegahaloundecapentaenoate, preferably in the form of the corresponding Grignard reagent, followed by hydrolysis of the product to form the α-substituted cyclohexanol and then dehydration to the cyclohexenyl compound. The side chain, i.e., the eleven carbon side chain can be formed piecemeal by suitable condensation employing the half aldehyde of a dicarboxylic acid of suitable carbon content to condense with a side chain of suitable carbon content with groups suitable to react with the aldehyde functional group.

A still further process can be used involving oxidation of derivatives of the desired undecapentaenoic acid with mild oxidants such as hypochlorite, e.g., sodium hypochlorite. The oxidants selected should preferably avoid secondary reactions with the remainder of the substrate molecule, or the oxidation should be carried out under controlled conditions to avoid appreciable secondary reactions, as by conducting oxidation with hypochlorite solution at or below about 10° C. and preferably between 0° and 5° C. For example, a compound of the formula

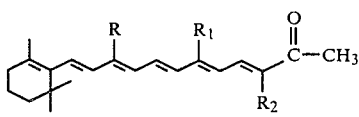

on oxidation with hypochlorite yields the corresponding acid of formula I herein. These new compounds can also be prepared by dehydration of corresponding α or β hydroxy acids or esters to form an alpha-beta ethylenic bond. The beta hydroxy acids or esters can be formed by condensation of an alpha-halo-carboxylic acid (or ester) with an aldehyde of two carbons less than the desired side chain in the presence of zinc (the Reformatsky Reaction).

The present compounds can also be prepared by oxidation of the corresponding aldehyde and alcohol of the same carbon content using oxidizing agents known for such reaction, e.g., hypochlorite, as previously described.

EXAMPLE 1

Ethyl 2,5,9-Trimethyl-11-(2,6,6-trimethyl-1-cyclohexen-1-yl)-2,4,6,8,10,-undecapentaenoate

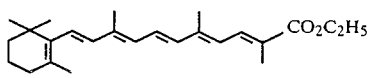

Sodium hydride (4.03 g, 50%) dispersion in mineral oil) was washed with dry pentane three times and suspended in 50 ml of anhydrous THF under nitrogen. The stirred mixture was cooled in an ice-water bath and 20.6 g of triethyl 2-phosphonopropionate was added dropwise. The resulting mixture was stirred for additional two hours while allowing the reaction mixture to warm up slowly to room temperature. The mixture was then cooled in an ice-water bath and a solution of retinal (16 g) in 50 ml of anhydrous THF was added dropwise. The resulting dark red mixture was stirred for four hours at room temperature; 700 ml of cold water was added and the mixture was extracted with three 200-ml portions of ether. The combined ethereal solution was washed with 100 ml of water and dried over sodium sulfate. Removal of solvent gave the crude ester (20 g, 97%) as a dark red oily substance. This material was used for the preparation of the free acid of Example 2 without further purification.

EXAMPLE 2

2,5,9-Trimethyl-11-(2,6,6-trimethyl-1-cyclohexen-1-yl)-2,4,6,8,10-Undecapentaenoic Acid

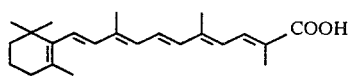

The crude ethyl ester (20 g) from Example 1 was dissolved in 50 ml of ethanol and a solution of potassium hydroxide (5.12 g) in 45 ml of ethanol and 5 ml of water was added dropwise with stirring under nitrogen. The resulting mixture was stirred for 12 hours at room temperature. The reaction mixture was partially concentrated under reduced pressure and then mixed with 500 ml of water. The resulting mixture was extracted with three 150 ml portions of ether. The ethereal layer was discarded, the aqueous layer was acidified to pH 3 with 10N aqueous hydrochloric acid. The resulting product was extracted into ether. The etheral solution was washed with water and dried over sodium sulfate. Concentration and filtration of this solution afforded the desired product as orange-red powders. Recrystallization in acetone/ethanol gave 9.3 g (50.6%) of pure product, mp 197°-199° C., UV spectrum (methanol) max 380 nm.

In like manner to the procedure described in Examples 1 and 2, the following compounds were prepared:

Ethyl 2-ethyl-5,9-dimethyl-11-(2,6,6-trimethyl-1-cyclohexen-1-yl)-2,4,6,8,10-undecapentaenoate (an oil);

Ethyl-2-propyl-5,9-dimethyl-11-(2,6,6-trimethyl-1-cyclohexen-1-yl)-2,4,6,8,10-undecapentaenoate (an oil);

2-Ethyl-5,9-dimethyl-11-(2,6,6-trimethyl-1-cyclohexen-1-yl)-2,4,6,8,10-undecapentaenoic acid (m.p. 162°-165° C.);

2-Propyl-5,9-dimethyl-11-(2,6,6-trimethyl-1-cyclohexen-1-yl)-2,4,6,8,10-undecapentaenoic acid (m.p. 172°-175° C.).

EXAMPLE 3A

Triethyl 2-Phosphonobutyrate

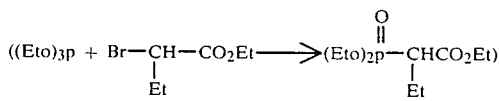

A mixture of ethyl 2-bromobutyrate (100 g, 0.5 mole and triethyl phosphite (85.2 g, 0.5 mole) was heated in an oil bath at 145° C. for 2 hrs. After cooling to room temperature, the reaction mixture was distilled at atmospheric pressure to remove the bulk of the ethyl bromide. The desired product was then distilled at 80°-95°

C. (0.15 mm of Hg). Obtained: 60 g of triethyl 2-phosphonobutyrate as colorless clear liquid.

EXAMPLE 3B 5,9-Dimethyl-2-Ethyl-11-(2.6,6-Trimethyl-1-Cyclohexen-1-yl)-2,4,6,8,10-Undecapentaenoic Acid

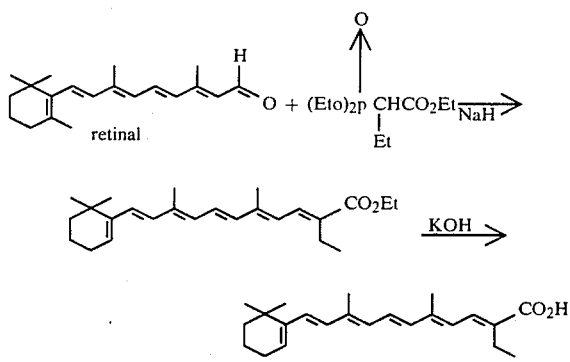

In analogy to the procedure given in Example 1: Triethyl 2-phosphonobutyrate was reacted with retinal to give ethyl 5,9-dimethyl-2-ethyl-11-(2,6,6-trimethyl-1-cyclohexen-1-yl)-2,4,6,8,10-undecapentaenoate, which was converted by the procedure of Example 2 to 5,9-dimethyl-2-ethyl-11-(2,6,6-trimethyl-1-cyclohexen-1-yl)-2,4,6,8,10-undecapentaenoic acid, m.p.=164°–165° C.

EXAMPLE 4A

Triethyl 2-Phosphonovalerate

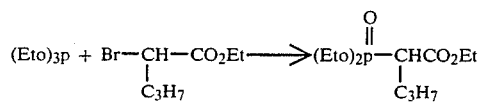

In analogy to the procedure given in Example 3: Ethyl 2-bromovalerate was treated with triethylphosphite to give triethyl 2-phosphonovalerate as a colorless clear liquid, b.p.=95°–110° C. (0.175 mm of Hg).

EXAMPLE 4B 5,9-Dimethyl-11-(2,6,6-Cyclohexen-1-yl)-2-Propyl-2,4,6,8,10-Undecapentaenoic Acid

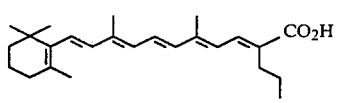

In analogy to the procedure described in Example 1: Triethyl 2-phosphonovalerate was reacted with retinal to give ethyl 5,9-dimethyl-11-(2,6,8-cyclohexen-1-yl)-2-propyl-2,4,6,8,10-undecapentaenoate, which was converted by the procedure of Example 2 to 5,9-dimethyl-11-(2,6,6-cyclohexen-1-yl)-2-propyl-2,4,6,8,10-undecapentaenoic acid, m.p.: 172°–175° C.

The compounds of this invention are active against various skin disorders, such as acne and psoriasis, when tested according to models considered to be predictive of the clinical condition in humans. The models used were the rhino mouse procedure (Kligman, et al., *J. Investigative Dermatology* 73, 354 (1979)), the rabbit comedolytic procedure (Mills OH, Kligman AM: Assay of Comedolytic Agents in the Rabbit Ear, Animal Models in Dermatology; Relevance to Human Dermatopharmacology and Dermatotoxicology, edited by H. I. Maibach, New York Churchill-Livingston, 1975, pp. 176-183) and the mouse epidermal cell culture procedure (Marcelo, et al., *J. Cell Biol.*, 79, 356 (1978). Testing was done comparatively against standard retinoids known to be effective in these disorders and against a known α-methyl retinoid (2,7-dimethyl-9-2,6,6-trimethyl-1-cyclohexene-1-yl-2,4,6,8-nonatetraenoic acid, referred to as DTCNA).

Activity equal to or greater than the standards and the known compound was shown by 2,5,9-trimethyl-11-(2,6,6-trimethyl-1-cyclohexene-1-yl)-2,4,6,8,10-undecapentaenoic acid (TTCUA). Thus, in the rabbit ear model at a concentration of 0.05%, it was equal to trans retinoic acid (TRA) in ability to reduce comedone size. In the rhino mouse model at the same concentration, it was equal to TRA in ability to reduce significantly the size of utriculi (pseudocomedones) and the amount of horny impaction in the utriculi. The skin of these mice showed moderate epidermal hyperplasia and significantly less wrinkling than the untreated control animals.

In the mouse epidermal cell culture at a concentration of 12 μg/ml, it reduced cell proliferation, as measured by inhibition of the uptake of tritiated thymidine into DNA. Table I shows percentage uptake relative to vehicle control (100%).

TABLE 1

| Day of Culture Exposure to Drug | TRA | CRA | TTCUA | DTCNA |
|---|---|---|---|---|
| 3 | 77 | 47 | 31 | 53 |
| 5 | 53 | 75 | 15 | 61 |
| 10 | 36 | 64 | 21 | 60 |

Percentage uptake with TTCUA is seen to be up to five fold less at all time points in comparison to both standards. Known compound DTCNA in contrast is seen to give about the same percentage uptake as the standard drugs at all three time points. Likewise TTCUA showed high anti-differentiation activity at 12 μg/ml in the mouse epidermal cell culture, as shown in Table II.

TABLE II

| Day of Culture Exposure to Drug | Vehicle Control | TRA | CRA | TTCUA | DTCNA |
|---|---|---|---|---|---|
| 3 | 3/6 | 3/5 | 2/7 | 2/6 | 3/6 |
| 6 | 3/5 | 3/5 | 2/7 | 0.5/8.5 | 2/6 |
| 10 | 7.5/2 | 2/6 | 2/6.5 | 1/7.5 | 2/5 |

The ratios in the table represent scoring of two measured parameters, culture staining by the Kreyberg technique (maximum differentiation 10) and nuclei enumeration (maximum differentiation 0). Thus the highest possible anti-differentiative activity would be given by the ratio 0/10. TTCUA is seen to be more active in both parameters than the two standards whereas the known compound is about the same as the standards.

Compounds of the present invention were found to have potent activity in regulating the formation of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicostetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5,12-diHETE are chemotactic for human neutrophils and eosinophils, and may augment the inflammation process. 5-HPETE is known to be a precursor of slow-reacting substance of anaphylaxis (SRS-A). The SRS family of molecules, such leukotrienes B, C, and D, have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL

A homogenate of human neutrophils containing lipoxygense activity is incubated for 5 minutes at 37° with $^{14}C$-arachidonic acid (AA). Citric Acid (2M) is used to quench the reaction. Following the addition of a trace amount of $^{3}H$-AA together with an excess of unlabeled AA to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets. The sheets are developed with an ethyl acetate/isooctane/water/acetic acid solvent system. The AA-spots are identified with iodine vapors, cut out and placed in scintillation vials for counting. After adjusting for the extraction efficiency, the amount (pmole) of $^{14}C$-AA in each of the tubes is quantitated. The pmoles of oxidized AA are obtained by subtracting the pmoles of AA remaining in the tubes containing active enzyme (control) from the pmoles of AA in the tubes acidified prior to the addition of enzyme (blank). The ability of the test compounds to modulate the activity of this enzyme is determined by an increase or decrease in the net amount of AA oxidized.

A representative compound of the invention

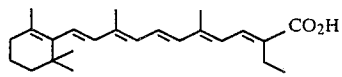

was found to require a concentration of 13 $\mu M$ ($I_{50}=13$ $\mu M$) to inhibit 50% of the enzyme.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

A convenient form for administration of the present new compounds are salts of those compounds in which $R_3$ is OH, particularly salts with alkali metals such as sodium and potassium, the ammonium salt and salts with organic amines, particularly those commonly employed in pharmaceutical formulations. The salts, of course, should be pharmaceutically-acceptable, that is the salt formation does not appreciably increase the toxicity of the therapeutic agent nor cause a toxic reaction in the host.

What is claimed is:

1. A therapeutic composition for the treatment of inflammatory conditions and allergic responses, in combination with at least one pharmaceutically-acceptable extender, at least one polyolefinic compound of the general formula

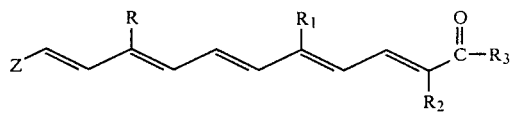

in which R and $R_1$ are each hydrogen or an alkyl group of from 1 to 5 carbon atoms; $R_2$ is an alkyl group of from 1 to 5 carbon atoms; $R_3$ is hydroxyl, alkoxy of from 1 to 5 carbon atoms, $NH_2$, $NHR_2$ or $NR_2R_2$ and Z is a cycloalkyl, cycloalkenyl or cycloalkdienly group substituted with from 0 to 5 alkyl groups, a keto group or a hydroxyl group or a phenyl group substituted with from 0 to 4 hydroxy, alkoxy, alkyl or trifluoromethyl groups or halogen atoms or combinations thereof and the pharmaceutically-acceptable salts thereof;

wherein said pharmaceutically—acceptable extender is in the form of tablets, capsules or solutions for oral administration; solutions for parenteral administration; dusting powders, aerosol sprays, ointments, creams and lotions for topical administration.

2. The therapeutic composition of claim 1 in which polyolefinic compound R is H or methyl, $R_1$ is methyl, $R_2$ is lower alkyl, $R_3$ is hydroxyl or alkoxy of from 1 to 5 carbon atoms and Z is a cycloalkenyl group with from 0 to 5 alkyl groups, or a phenyl group substituted with from 0 to 4 alkoxy or alkyl groups of from 1 to 5 carbon atoms or a combination thereof.

3. The therapeutic composition of claim 2 in which polyolefinic compound Z is the group 2,6,6-trimethyl-1-cyclohexen-1-yl.

4. The therapeutic composition of claim 3 in which the polyolefinic compound is ethyl 2,5,9-trimethyl-11-(2,6,6-trimethyl-1-cyclohexen-1-yl)-2,4,6,8,10-undecapentaenoate.

5. The therapeutic composition of claim 3 in which the polyolefinic compound is 2,5,9-trimethyl-11-(2,6,6-trimethyl-1-cyclohexen-1-yl)-2,4,6,8,10-undecapentaenoic acid.

6. The therapeutic composition of claim 3 in which the polyolefinic compound is ethyl 2-ethyl-5,9-dimethyl-11-(2,6,6-trimethyl-1-cyclohexen-1-yl)2,4,6,8,10-undecapentaenoate.

7. The therapeutic composition of claim 3 in which the polyolefinic compound is ethyl-2-propyl-5,9-dimethyl-11-(2,6,6-trimethyl-1-cyclohexen-1-yl)-2,4,6,8,10-undecapentaenoate.

8. The therapeutic composition of claim 3 in which the polyolefinic compound is 2-ethyl-5,9-dimethyl-11-(2,6,6-trimethyl-1-cyclohexen-1-yl)-2,4,6,8,10-undecapentaenoic acid.

9. The therapeutic composition of claim 3 in which the polyolefinic compound isd 2-propyl-5,9-dimethyl-11-(2,6,6-trimethyl-1-cyclohexen-1-yl)-2,4,6,8,10-undecapentaenoic acid.

10. A method for treating inflammatory conditions and allergic responses in a human host which comprises administering to said host a therapeutically effective amount of at least one polyolefinic compound of the general formula

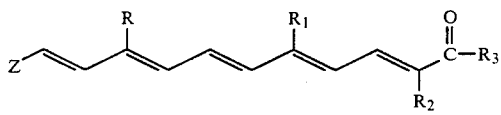

in which R and R$_1$ are each hydrogen or an alkyl group of from 1 to 5 carbon atoms; R$_2$ is an alkyl group of from 1 to 5 carbon atoms; R$_3$ is hydroxyl, alkoxy of from 1 to 5 carbon atoms, NH$_2$, NHR$_2$ or NR$_2$R$_2$ and Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl or trifluoromethyl groups or halogen atoms or combinations thereof and the pharmaceutically-acceptable salts thereof.

11. The method of claim 10 in which R is H or methyl, R$_1$ is methyl, R$_2$ is lower alkyl, R$_3$ is hydroxyl or alkoxy of from 1 to 5 carbon atoms and Z is cycloalkenyl group with from 0 to 5 alkyl groups, or a phenyl group substituted with from 0 to 4 alkoxy or alkyl groups of from 1 to 5 carbon atoms or a combination thereof.

12. The method of claim 10 in which Z is the group 2,6,6-trimethyl-1-cyclohexen-1-yl.

13. The method of claim 12 in which the polyolefinic compound compound is ethyl 2,5,9-trimethyl-11-(2,6,6-trimethyl-1-cyclohexen-1-yl)-2,4,6,8,10-undecapentaenoate.

14. The method of claim 12 in which the polyolefinic compound is 2,5,9-trimethyl-11-(2,6,6-trimethyl-1-cyclohexen-1-yl)-2,4,6,8,10-undecapentaenoic acid.

15. The method of claim 12 in which the polyolefinic compound is ethyl 2-ethyl-5,9-dimethyl-11-(2,6,6-trimethyl-1-cyclohexen-1-yl)-2,4,6,8,10-undecapentaenoate.

16. The method of claim 12 in which the polyolefinic compound is ethyl-2-propyl-5,9-dimethyl-11-(2,6,6-trimethyl-1-cyclohexen-1-yl)-2,4,6,8,10-undecapentaenoate.

17. The method of claim 12 in which the polyolefinic compound is 2-ethyl-5,9-dimethyl-11-(2,6,6-trimethyl-1-cyclohexen-1-yl)-2,4,6,8,10-undecapentaenoic acid.

18. The method of claim 12 in which the polyolefinic compound is 2-propyl-5,9-dimethyl-11-2,6,6-trimethyl-1-cyclohexen-1-yl)-2,4,6,8,10-undecapentaenoic acid.

* * * * *